(12) United States Patent
Tange

(10) Patent No.: US 7,089,801 B2
(45) Date of Patent: Aug. 15, 2006

(54) METAL RING INSPECTION METHOD AND METAL RING INSPECTION DEVICE

(75) Inventor: Hiroshi Tange, Fuji (JP)

(73) Assignee: JATCO Ltd, (JP)

( * ) Notice: Subject to any disclaimer, the term of this patent is extended or adjusted under 35 U.S.C. 154(b) by 0 days.

(21) Appl. No.: 11/111,880

(22) Filed: Apr. 22, 2005

(65) Prior Publication Data

US 2005/0241406 A1 Nov. 3, 2005

(30) Foreign Application Priority Data

Apr. 27, 2004 (JP) ............................. 2004-131153

(51) Int. Cl.
*G01N 3/08* (2006.01)
*G01M 19/00* (2006.01)
(52) U.S. Cl. ........................................ 73/818; 73/865.8
(58) Field of Classification Search ................ 73/818, 73/865.8; 474/8
See application file for complete search history.

(56) References Cited

U.S. PATENT DOCUMENTS 6,612,954 B1 * 9/2003 Akagi et al. ................. 474/242
6,684,473 B1 * 2/2004 Yamagishi et al. ...... 29/407.01
6,779,414 B1 * 8/2004 Shori et al. ................. 73/865.9
6,949,013 B1 * 9/2005 Suzuki ......................... 451/66

FOREIGN PATENT DOCUMENTS

| JP | 09-304288 | 11/1997 |
|---|---|---|
| JP | 11-248637 | 9/1999 |
| JP | 2002-116113 A | 4/2002 |
| JP | 2002-148146 A | 5/2002 |
| JP | 2004-101240 A | 4/2004 |

OTHER PUBLICATIONS

Netherlands Search Report, Dec. 7, 2005.

* cited by examiner

*Primary Examiner*—Max Noori
*Assistant Examiner*—Octavia Davis
(74) *Attorney, Agent, or Firm*—Blank Rome LLP

(57) ABSTRACT

A metal ring inspection method of a Continuously Variable Transmission (CVT) V-belt for inspecting end face defects in a belt laminated band composed of a plurality of metal ring stacked layers in which a first process is executed which grasps the outer periphery surface of the belt laminated band from both sides to firmly touch the inner periphery surface and removes crowning from the metal rings; a second process is executed which applies a sliding force in the width direction relative to each metal ring constituting the belt laminated band to expose the belt laminated band end face in a different tiered shape; and subsequently a third process is executed which inspects the belt laminated band end face defects exposed in the different tiered shape.

9 Claims, 13 Drawing Sheets

PRIOR ART

PRIOR ART

PRIOR ART

METAL RING INSPECTION METHOD AND METAL RING INSPECTION DEVICE

BACKGROUND OF THE INVENTION

1. Field of the Invention

The present invention relates to a metal ring inspection method and a metal ring inspection device for performing defect inspection of a metal ring which is one of the components that constitute a V-belt type of a Continuously Variable Transmission belt (hereinafter denoted as "CVT belt") mounted in a vehicle, such as an automobile.

2. Description of the Related Art

Conventionally, there is a known CVT belt structure which laminates a plurality of thin metal rings in a stack of approximately 0.2 mm in thickness to which steel elements are consecutively attached.

FIG. 11A is an outline view of a CVT belt. In this diagram, a CVT belt 1 is constructed by assembling two laminated bands 2 of a layered belt that contain a stack of a number of metal rings 2a (for example, a laminated band composed of about 12 endless layers) which are supported by a layered element 3 composed of a large number of steel elements 3a (for example, about 400 elements).

In this manner, the structure of the CVT belt 1 is produced through the following processes:

(a) First, a ring-shaped drum is formed by welding together the ends of a thin sheet of ultra high strength steel, such as maraging steel.

(b) Next, the drum is cut into round slices of a predetermined width and rolled to create metal rings 2a of a basic peripheral length.

(c) Next, after performing a solution treatment, etc. to each of the above-mentioned metal rings 2a, a peripheral length correction process is performed that provides the necessary peripheral length corresponding to the lamination location on the CVT belt 1. Here, "peripheral length" means the circumference length of the metal rings 2a. The peripheral lengths of the metal rings 2a are subtly different for each lamination stacked position in the CVT belt 1. For example, the outermost periphery side is slightly longer and the innermost periphery side is slightly shorter.

(d) Subsequently, while inspecting whether or not the appropriate peripheral length for each stacked layer position is within specification limits using a peripheral length measuring device, the presence of surface defects in the metal rings 2a is inspected using a metal ring inspection device.

(e) After performing aging treatment, nitride treatment, etc. to increase surface hardness of the metal rings 2a which passed a quality control inspection, the metal rings 2a with the appropriate peripheral length difference applied for each layer are sequentially laminated together to form a belt laminated band 2. The steel elements 3a are consecutively attached and the CVT belt 1 is completed.

As described previously, the belt laminated band 2 of the CVT belt 1 is composed of a stack of about 12 layers of the metal rings 2a.

FIG. 11B is a stacked layer state view of the belt laminated band 2. In this diagram, when the stacked layer sheet number of the metal rings 2a is defined as n, 2a (1) represents the metal ring positioned on the innermost side (hereinafter, denoted as "innermost periphery layer"), 2a (n) represents the metal ring positioned on the outermost side (hereinafter, denoted as "outermost periphery layer") and 2a (2)~2a (n−1) represent the metal rings positioned in between the innermost and outermost sides.

FIG. 11C is an outline diagram of the metal rings 2a. Each of the metal rings 2a has what is called a crowning shape which is slightly arched in the ring inner periphery surface and has a springy nature acquired through the aging treatment in conjunction with the heat treatment.

FIG. 11D is a diagram showing the end face shape of the metal rings 2a. As illustrated in this view, the end face of each of the metal rings 2a constitutes a smooth shape in which the angle declines (slightly curved).

The "metal ring inspection device" is an apparatus which inspects for the presence of surface defects in the metal rings 2a before being assembled together in stacked layers. Also, while the metal rings 2a containing a defect are rejected as defective parts, the metal rings 2a containing no imperfections or those which have a level of small flaws or superficial flaws that can be ignored are non-defective parts and assembled in stacked layers to form a CVT belt 1.

FIG. 12 is a conceptual configuration diagram of a conventional prior art device applicable to the above-described "metal ring inspection device" for example as disclosed in Japanese Laid-Open Patent Application No. H11-248637 (1999) titled "DEFECT DETECTING DEVICE" (hereinafter, denoted as "conventional prior art device"). This conventional prior art device comprises a plurality of the light guiding paths 6a~6c composed of a plurality of optical fibers for guiding irradiated light which travels unidirectionally from the inspection light source 4 to the inspectable surface 5. Also, at least two light guiding paths 8a and 8b (optical fiber) are arranged alternately in between the light guiding paths 6a~6c for guiding the reflected light Pf and Pg from the inspectable surface 5 to the light reception segments 7a and 7b. Noteworthy is the spacing arrangement of the two light guiding paths 8a and 8b which are separated at a slight distance L.

In such a configuration, when an inspectable surface 5 does not have a defect, such as a flaw, etc., the reflected light Pf and Pg guided by the two light guiding paths 8a and 8b is supplied to the light reception segments 7a and 7b at substantially the same intensity. On the other hand, when an inspectable surface 5 has a defect, since there is a decline (light intensity decline by diffused reflection) in the reflected light of an applicable defective part, a difference occurs in the light of the light guiding paths 8a and 8b and the existence of a defect can be automatically discriminated from the amount of this difference. Consequently, by using the surface of the metal rings 2a as the above-stated inspectable surface 5, this concept can be applied to the inspection device of the metal rings 2a for the CVT belt 1, for example, the metal ring inspection device.

However, because the conventional prior art metal ring inspection device cannot inspect the metal rings 2a which are the object to be inspected as one component at a time, this device has poor inspection efficiency.

Here, if attention is directed to the defect "end face" of the metal rings 2a and since the ring end faces exposed on the outer section are also in a stacked layer state, by including this exposed surface into the above-stated inspectable surface 5 a batch inspection for metal ring end face defects in the stacked layers could be performed. Although supposed that an improvement in inspection efficiency can be achieved, because the expected inspection accuracy is not actually acquired there is no efficiency improvement.

FIGS. 13A and 13B are explanatory diagrams of the conventional prior art disadvantages. The visual line 9 shows the observation direction of the metal rings 2a end faces. This observation direction is equivalent to the incidence direction of the reflected light Pf and Pg to the light reception segments 7a and 7b in the conventional prior art (refer to FIG. 12). As stated above, the metal rings 2a end faces have a smooth form without the angle. For this reason as shown in FIG. 13A, when the end faces are observed from an angle (at a slant), a shadow (dashed line circles) will occur in some of the metal rings 2a end faces in a stacked layer state and a defect in the shadow portions will be overlooked. Additionally as shown in FIG. 13B when the metal rings 2a end faces in a stacked layer state are irregularly (unevenly) constituted, a larger shadow (dashed line circle) occurs and a defect of an even larger scope will be overlooked.

Thus, in a batch inspection of the metal rings 2a end faces in a stacked layer state using merely the above-mentioned conventional prior art device, sufficient accuracy cannot be acquired and an improvement in the inspection efficiency cannot be achieved.

Therefore, the object of the present invention is to provide a metal ring inspection method and a metal ring inspection device capable efficiently inspecting metal ring end faces as a batch (collectively) for defects in a stacked layer state.

SUMMARY OF THE INVENTION

In the present invention, a metal ring inspection method of a Continuously Variable Transmission (CVT) V-belt for inspecting end face defects in a belt laminated band is composed of a plurality of metal ring stacked layers in which a first process is executed which grasps the outer periphery surface of the belt laminated band from both sides to firmly touch the inner periphery surface and removes crowning from the metal rings; a second process is executed which applies a sliding force in the width direction relative to each metal ring constituting the belt laminated band to expose the end face of the belt laminated band in an different tiered shape; and a third process is subsequently executed which inspects the belt laminated band end face defects exposed in a different tiered shape.

Additionally, according to the present invention a metal ring inspection device of a Continuously Variable Transmission (CVT) V-belt for inspecting end face defects in a belt laminated band is composed of a plurality of metal ring stacked layers comprising a crowning removal means which grasps the outer periphery surface of the belt laminated band from both sides so as to be firmly in contact with the inner periphery surface and removes crowning from the metal rings; an end face exposure means which applies a sliding force in the width direction relative to each metal ring after crowning removal and exposes the belt laminated band end face in an different tiered shape; and an inspection means which inspects the belt laminated band end face defects exposed in an different tiered shape.

Furthermore, in the preferred embodiments of the metal ring inspection device in the present invention, the crowning removal means removes crowning from the metal rings with a configuration including a plurality of rollers situated around the belt laminated band in which the position of each roller is shifted to increase pressure applied to the outer periphery surface of the belt laminated band.

According to the preferred embodiments of the present invention, the crowning removal means removes crowning from the metal rings with a configuration including at least a pair of rollers which grasp and rotate between the belt laminated band to increase the pressing force between a pair of rollers.

Further, in the preferred embodiments of the present invention, the end face exposure means has a configuration including at least a pair of ring end face presser bars which abut with both sides of the laminated band to adjust the angle of these ring end face presser bars and apply a sliding force in the width direction relative to each metal ring after crowning removal to expose the belt laminated band end face in a different tiered shape.

In addition, in the preferred embodiments of the present invention, the end face exposure means has a configuration including a taper formed in at least one pair of rollers which grasp and rotate between the belt laminated band according to the relative movement of the taper and apply a sliding force in the width direction relative to each metal ring after crowning removal to expose the belt laminated band end face in a different tiered shape.

According to the present invention, each end face of the belt laminated can be extensively exposed in a different tiered shape while applying pressure (refer to Pa, Pb of FIG. 1) from both sides to remove crowning and applying a sliding force (refer to Pc, Pd of FIG. 3) in the width direction by grasping the laminated band with a person's fingertips. As a result in this different tiered state, since the portions (refer to the dotted line circles in FIG. 13) which constitute end face shadows are diminished, end face inspection by visual observation of the belt laminated band can be performed efficiently en masse.

Based on the preferred embodiments of the present invention, each process of crowning removal in the belt laminated band, exposure of the end faces in a different tiered shape and end face defect inspection is automated.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

BRIEF DESCRIPTION OF THE DRAWINGS

FIG. 11 is an outline view of a CVT belt showing a diagram of the belt laminated band 2 in a stacked layer state, an outline diagram of the metal rings 2a and the end face shape of the metal rings 2a.

DETAILED DESCRIPTION OF THE PREFERRED EMBODIMENTS

The preferred embodiments of the present invention will hereinafter be described in detail with reference to the drawings. Additionally, illustration of specific or example numerical values for various details in the following explanation or character strings and other symbols are merely references to clarify the concept of the present invention. Accordingly, the concept of the present invention should not be limited explicitly to this terminology entirely or in part.

In addition, explanation is omitted which describes details of well-known methods, well-known procedures, well-known architecture, well-known circuit configurations, etc. (hereinafter denoted as "common knowledge") for the purpose of concise explanation, but does not intentionally exclude this common knowledge entirely or in part. Therefore, relevant common knowledge already known by persons skilled in the art at the time of filing the present invention is naturally included in the following description.

First Embodiment

Figure 2A:
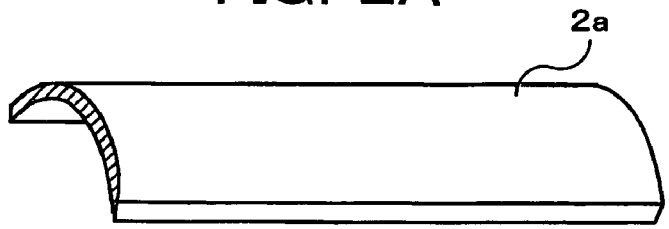
FIG. 2 is a principle diagram of the first embodiment.
Figure 2B:
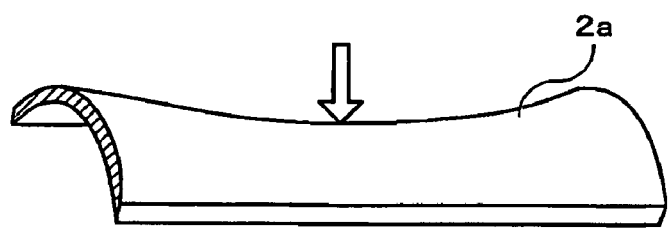
Figure 2C:
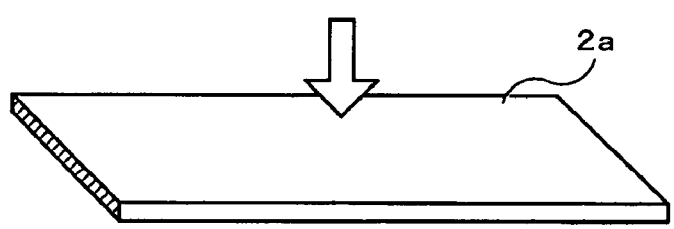
Figure 2D:
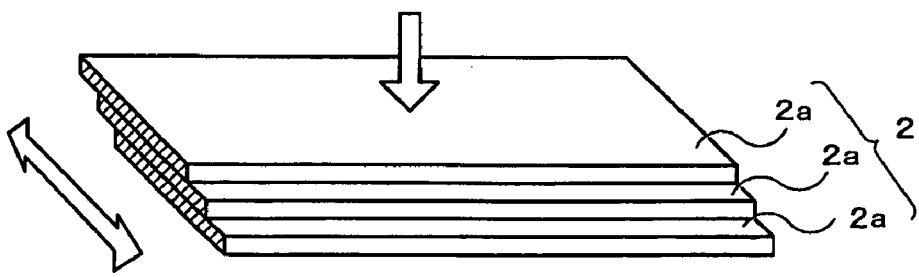
Figure 3A:
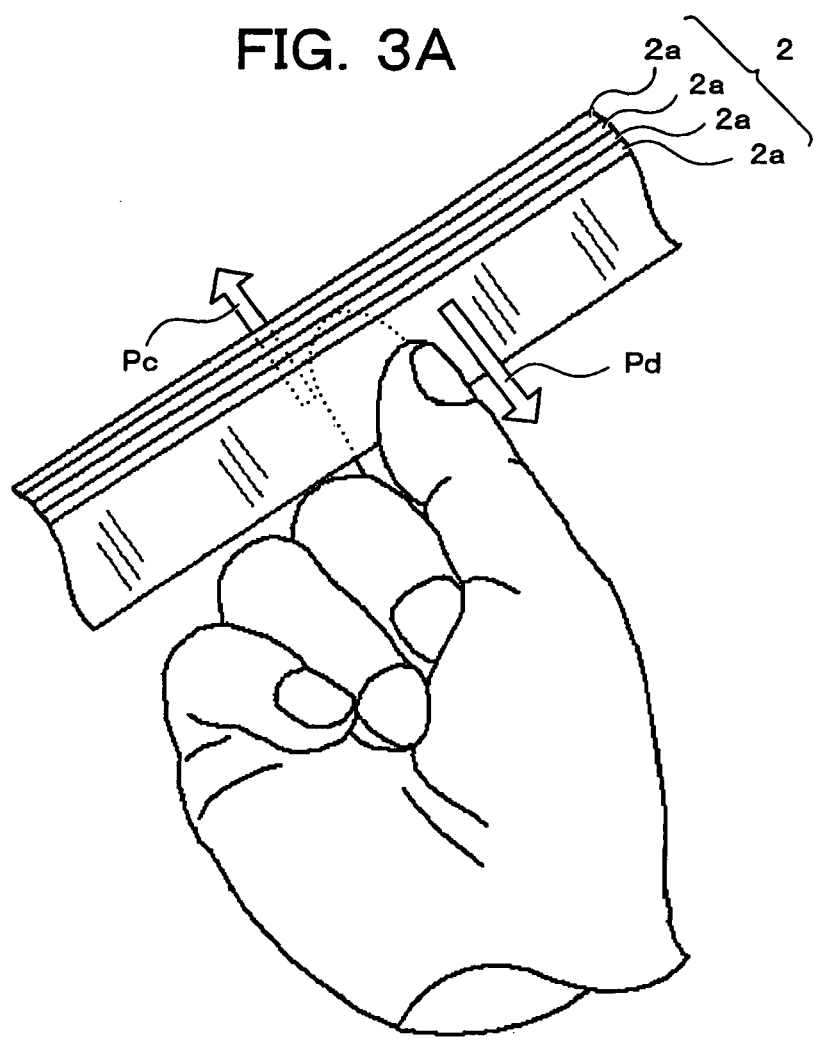
FIG. 3 is the second and third process drawings of the first embodiment.
Figure 3B:
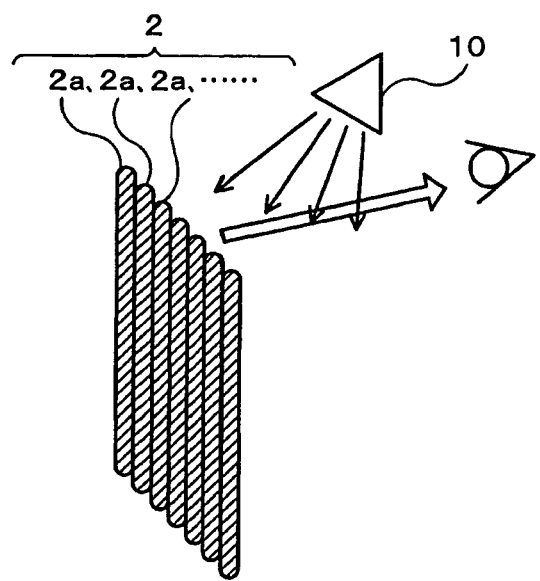

FIGS. 1~3 show the embodiment of the "metal ring inspection method" (hereinafter denoted as the "first embodiment") related to the present invention.

Figure 1A:
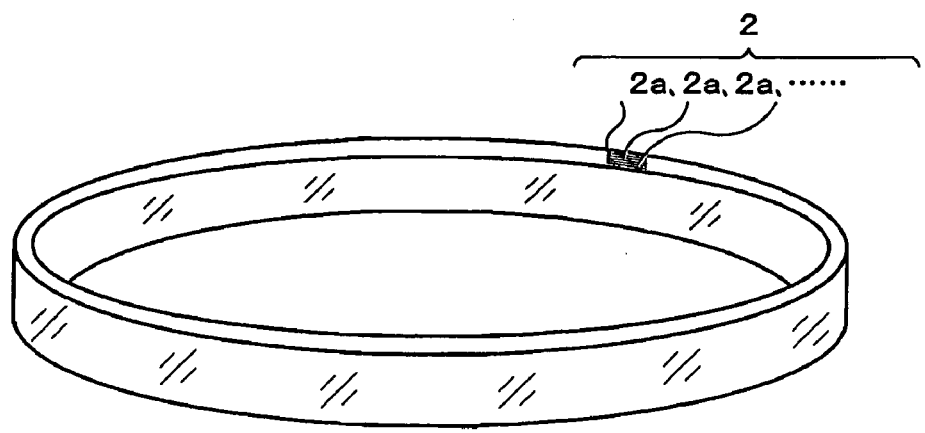
FIG. 1 is the first process drawing of the first embodiment.
Figure 1B:
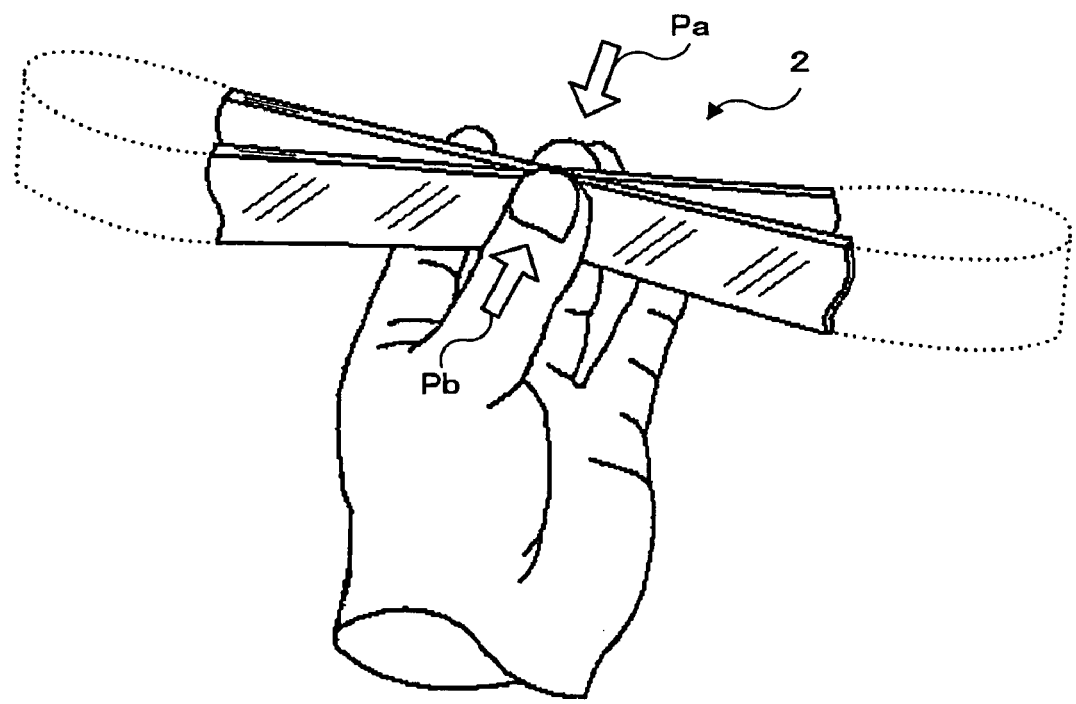

Initially, in a first process, a stacked layer of n sheets of the metal rings 2a which constitute the objects to be inspected are formed as a belt laminated band 2 (refer to FIG. 1A). The outer periphery surface of the belt laminated band 2 is grasped with a person's fingertips from both sides and pressure Pa, Pb is applied to firmly touch (in contact with) the inner periphery surface (refer to FIG. 1B).

Here, as mentioned in the beginning the metal rings 2a have a crowning shape (refer to FIG. 2A) and thus do not easily "slide sideways" in a stacked layer state. By applying pressure Pa, Pb (refer to FIG. 2B) so as to firmly touch the inner periphery surface as stated above, this crowning can be temporarily removed and altered into a substantially level surface (refer to FIG. 2C). Furthermore, as the metal rings 2a have a springy nature this flat deformation will extend to the perimeter of the metal rings 2a.

Consequently, although the metal rings 2a are altered substantially level to the perimeter in a stacked layer state, they can be readily shifted (in a sliding type movement) (refer to FIG. 2D). In a second process as shown in FIG. 3A, the belt laminated band 2 is grasped from both sides with a person's fingertips and a sliding force Pc, Pd is applied in the width direction. In a third process while maintaining this shifted state (slightly twisted), light from a light source 10 is applied to the end faces to observe the reflective behavior. In this manner, the presence of end face defects can be inspected en masse (i.e., a batch inspection for a group of end faces).

Figure 13A:
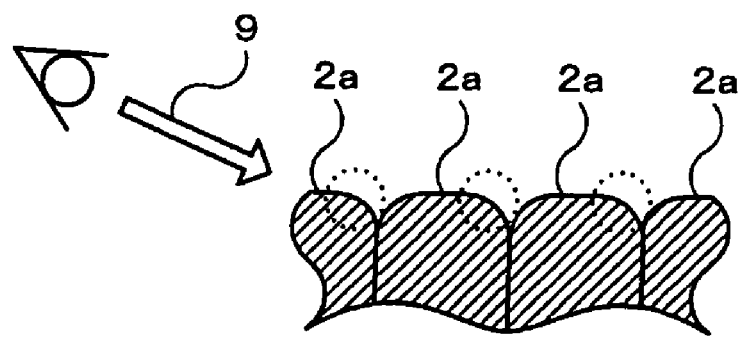
FIGS. 13A and 13B are explanatory diagrams of the conventional prior art disadvantages.
Figure 13B:
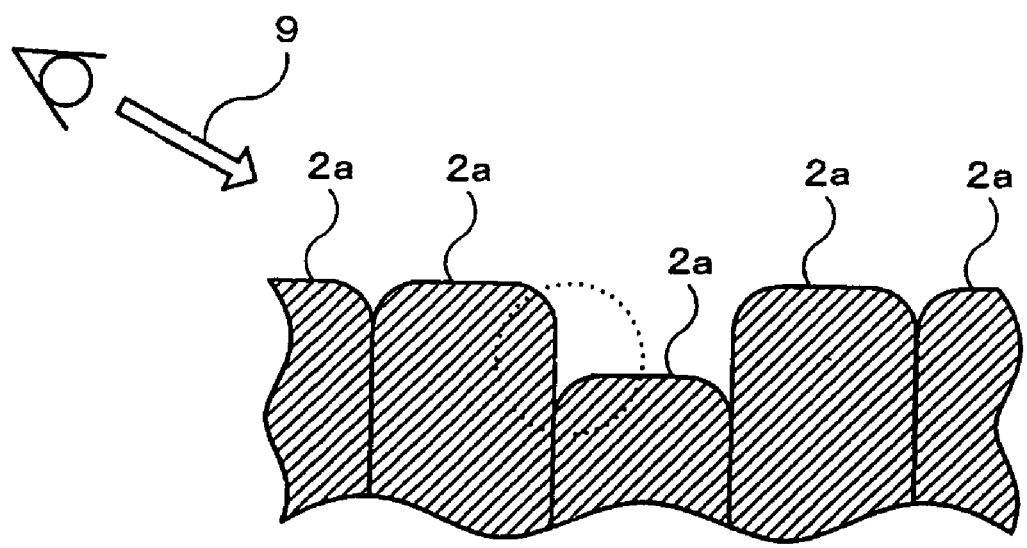

Thus, in the first embodiment while grasping the belt laminated band 2 with a person's fingertips and applying the pressure Pa, Pb from both sides to remove crowning, by adding the sliding force Pc, Pd in the width direction, each end face can be exposed extensively in a different tiered state. As a result in this different tiered state, since the portions (refer to the dotted line circles in FIG. 13) which constitute end face shadows are diminished, an end face inspection by visual observation of the belt laminated band 2 can be performed efficiently en masse.

Second Embodiment

Figure 4:
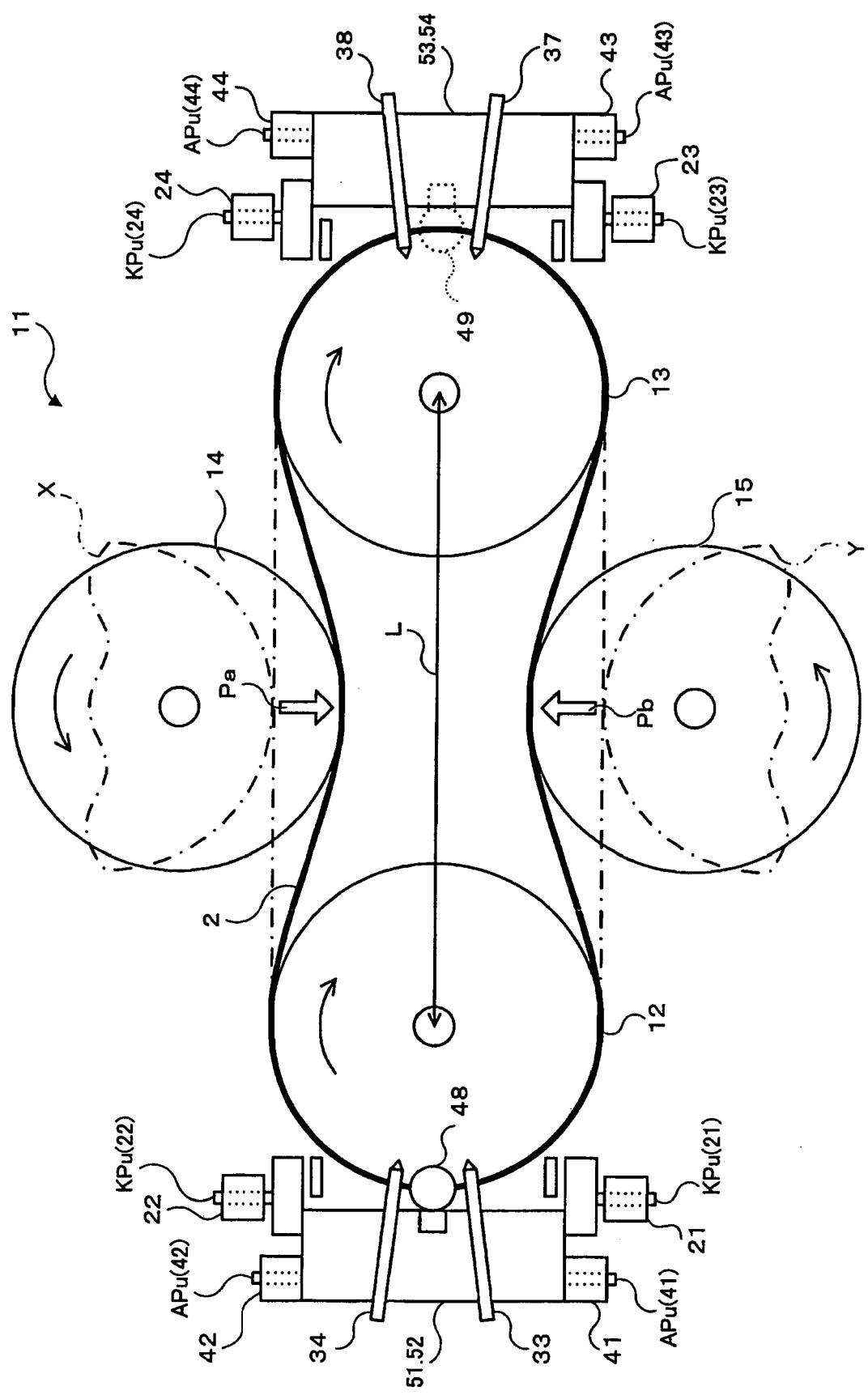
FIG. 4 is a top view of the second embodiment.
Figure 5:
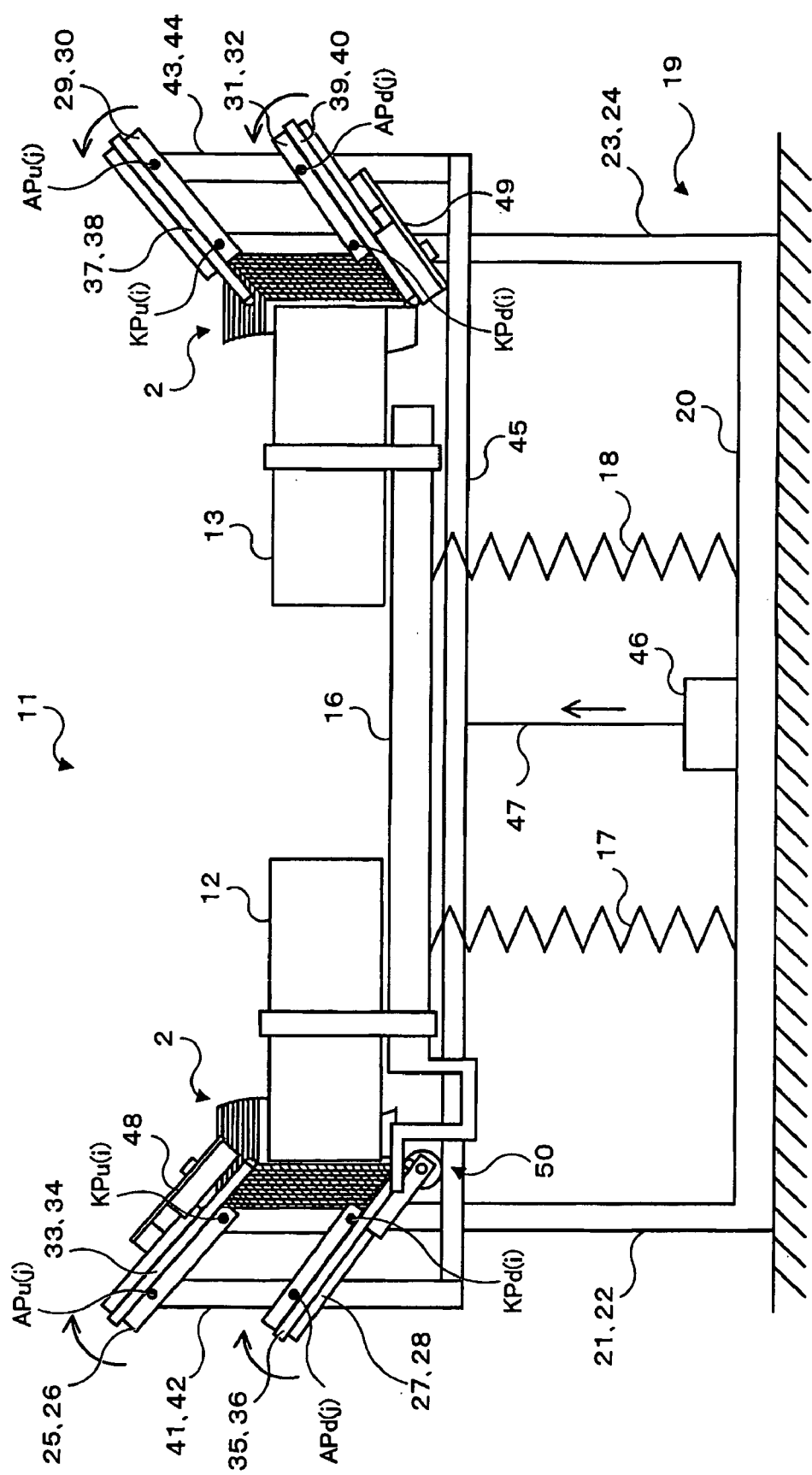
FIG. 5 is a side view of the second embodiment.
Figure 6:
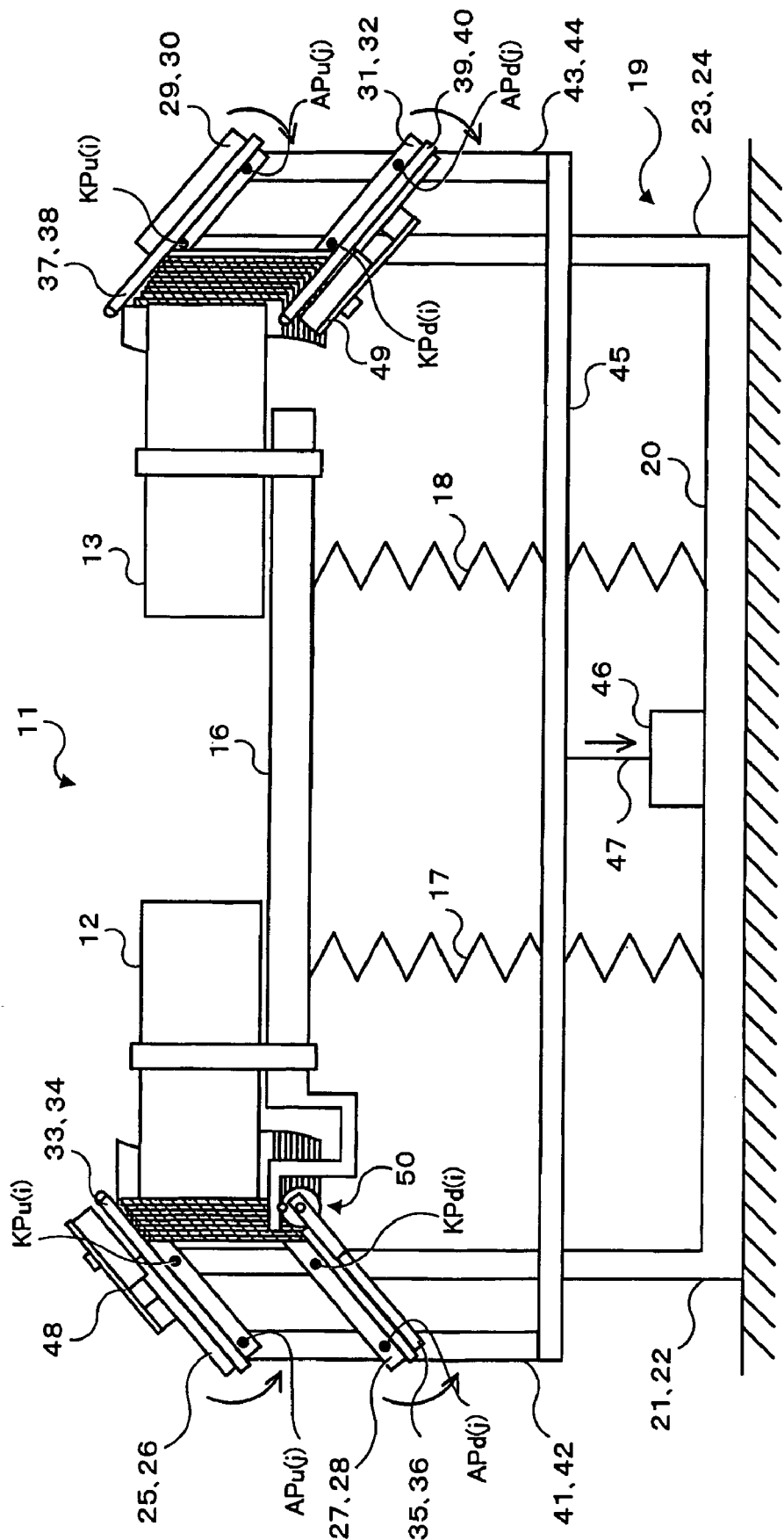
FIG. 6 is a side view of the second embodiment.

FIGS. 4~6 are diagrams showing the embodiment (hereinafter denoted as the "second embodiment") of the "metal ring inspection device" related to the present invention. FIG. 4 is a top view and FIGS. 5~6 are side views.

As positioned in the diagram of FIG. 4, the metal ring inspection device 11 comprises a left and right pair of inner periphery rollers 12, 13 (crowning removal means) which hold and rotate the inner periphery surface of the belt laminated band 2 composed of a laminated band with n sheets of the metal rings 2a; and a top and bottom pair of outer periphery rollers 14, 15 (crowning removal means) which hold and rotate the outer periphery surface of the same belt laminated band 2.

The rotational axis position of each of the inner periphery rollers 12, 13 is fixed. The center distance L constitutes a suitable distance which can mount the belt laminated band 2 on the inner periphery rollers 12, 13. On the other hand, the rotational axis position of the outer periphery rollers 14, 15 can migrate between two positions of an initial position and an inspection position.

The "initial position" is the position which does not become an obstacle at the time of mounting the belt laminated band 2 on the inner periphery rollers 12, 13, for example, the positions shown with the dashed dotted lines X and Y. Furthermore, the "inspection position" is the position which can apply the required pressure from both directions relative to the outer periphery surface of the belt laminated band 2 in a mounted state on the inner periphery rollers 12, 13, for example, the present position of the outer periphery rollers 14, 15 shown with continuous lines.

As seen in the diagram, when the outer periphery rollers 14, 15 are in the inspection position, the pressure Pa (equivalent to the suppressing strength of the pressure Pa with a person's fingers in the first embodiment) is applied to the outer periphery surface in the upper direction diagram of the belt laminated band 2 for one direction of the outer periphery roller 14. Also, the pressure Pb (equivalent to the suppressing strength of the pressure Pb with a person's fingers in the first embodiment) is applied to the outer periphery surface in the lower direction diagram of the belt laminated band 2 for the other direction of the outer periphery roller 15.

As stated above, because each of the metal rings 2a which constitute the belt laminated band 2 has a crowning shape (refer to FIG. 2A), the metal rings 2a do not easily "slide sideways" in a stacked layer state. Also, as described earlier, crowning can be temporarily removed by applying the required pressure Pa, Pb from both sides relative to the outer periphery surface of the belt laminated band 2 and can be altered into a substantially level surface. In addition, as the metal rings 2a have a springy nature this flat deformation will extend to the perimeter of the belt laminated band 2 in a mounted state on the inner periphery rollers 12, 13.

Accordingly, when the metal ring inspection device 11 is configured as in the diagram, the pressure Pa, Pb can be applied to the outer periphery surface of the belt laminated band 2 mounted on the inner periphery rollers 12, 13 by moving the outer periphery rollers 14, 15 from their initial position to the inspection position. In this manner, crowning can be removed and automation of the first process in the first embodiment can be achieved.

Also, in the foregoing first embodiment, after removal of the crowning in the metal rings 2a according to the first process, the second process shifts the metal rings 2a in a stacked layer state and exposes extensively the end faces in a different tiered state. Subsequently, the third process is executed to inspect the exposed end face defects in terms of a batch. Like the first process above, these second and third processes can also be performed in the metal ring inspection device 11 in the diagram.

As seen in FIGS. 5 and 6, the inner periphery rollers 12, 13 are attached to a frame 16 for the inner periphery rollers. The frame 16 for the inner periphery rollers is pulled in the direction of the base 20 within the body frame 19 by the springs 17, 18. Besides, when the dead weight of the frame 16 for the inner periphery rollers is sufficiently heavy, the springs 17, 18 can be omitted.

The fixed pillars 21~24 are installed upright by the four corners of the base 20 in the body frame 19. Also, two pivots for every pillar are provided in each of the fixed pillars 21~24, respectively. Specifically, an upper side pivot KPu (i) and a lower side pivot KPd (i) are provided near the upper end of the fixed pillars 21~24 and in positions to a certain extent lower than the upper end, respectively.

Here, i is the number of the fixed pillars 21~24. Namely, the 1$^{st}$ fixed pillar 21 contains an upper side pivot KPu (21) and a lower side pivot KPd (21). Similarly, the 2$^{nd}$ fixed pillar 22 contains an upper side pivot KPu (22) and a lower side pivot KPd (22). The 3$^{rd}$ fixed pillar contains an upper side pivot KPu (23) and a lower side pivot KPd (23). The 4$^{th}$ fixed pillar contains an upper side pivot KPu (24) and a lower side pivot KPd (24).

The pivots KPu(i), KPd(i) are rockably attached to eight plates 25~32 on one end side. The ring end face presser bars 33~40 (end face exposure means) are attached to each of the plates 25~32.

Additionally, the other end side of the plates 25~32 are provided in movable pillars 41~44 and rockably attached to two pivots APu(j), APd(j) for every pillar, respectively.

Specifically, the 1$^{st}$ movable pillar 41 contains an upper side pivot APu (41) and a lower side pivot APd (41). Similarly, the 2$^{nd}$ movable pillar 44 contains an upper side pivot APu (42) and a lower side pivot APd (42). The 3$^{rd}$ movable pillar 43 contains an upper side pivot APu (43) and a lower side pivot APd (43). The 4$^{th}$ movable pillar 44 contains an upper side pivot APu (44) and a lower side pivot APd (44).

The four movable pillars 41~44 constitute left and right pairs as seen in the diagrams. A link 45 for horizontal angular adjustment is provided for connecting these companion pairs of movable pillars (movable pillar 41 and movable pillar 43; movable pillar 42 and movable pillar 44). A shaft 47 of an up-and-down drive mechanism 46 composing a servo, etc. is connected near the central part of this link 45 for angular adjustment. The link 45 for angular adjustment can move definably between the "uppermost position" as shown in FIG. 5 to the "lowermost position" as shown in FIG. 6.

On the upper surface of the plates 25, 26 in the left-hand side of the drawing, the 1$^{st}$ end face defect inspection part 48 is attached facing downward to the inspectable surface. Also, on the lower surface of the plates 31, 32 in the right-hand side of the drawing, the 2$^{nd}$ end face defect inspection part 49 is attached facing upward to the inspectable surface. The 1$^{st}$ end face defect inspection part 48 is a device which inspects en masse (in a group) the upper side end face defects toward the drawing of the belt laminated band 2 composing stacked n sheets of the metal rings 2a. Similarly, the 2$^{nd}$ end face defect inspection part 49 is a device which inspects en masse the lower side end face defects toward the drawing of the same belt laminated band 2. These 1$^{st}$ and 2$^{nd}$ end face defect inspection parts 48, 49, for example, adapted the technique disclosed in the conventional prior art device mentioned above. Besides, a cam roller 50 for inner periphery roller positioning is attached to the lower surface of the plates 27, 28 in the left-hand side of the drawing. This cam roller 50 for inner periphery roller positioning touches the lower surface of the frame 16 for the inner periphery roller at the position of the innermost periphery ring lower end surface on the outer side of the belt laminated band 2 and also performs positioning of the frame 16 for the inner periphery roller.

Furthermore, the eight plates 25~32 constitute two respective groups (one group represents plate 25, plate 26, plate 27 and plate 28; and the second group represents plate 29, plate 30, plate 31 and plate 32). The companion plates of these groups are unified by the connection members 51~54 (refer to FIG. 4). Specifically, between plate 25 and plate 26 are unified by the connection member 51, between plate 27 and plate 28 are unified by the connection member 52, between plate 29 and plate 30 are unified by the connection member 53 and between plate 31 and plate 32 are unified by the connection member 54.

In this embodiment of the metal ring inspection device 11 having such a configuration as seen in the FIG. 5 stage, when the shaft 47 of the up-and-down drive mechanism 46 is expanded to the maximum, the link 45 for angular adjustment moves to the "uppermost position." Because the four movable pillars 41~44 are installed upright by both sides of the link 45 for angular adjustment and follow the upward movement of the link 45 for angular adjustment, these movable pillars 41~44 also move in the same direction.

The pivots APu(j) and APd(j) are respectively provided in the movable pillars 41~44 and one end side of the plates 25~32 is attached to the freely rotatable pivots APu(j) and APd(j). Further, since the other end side is respectively supported by the freely rotatable pivots KPu(i) and KPd(i) of the fixed pillars 21~24, ultimately the plates 25~32 will rotate in the axis of the fixed side pivot points APu(j) and APd(j) following the upward movement of the movable pillars 41~44.

Namely, when the shaft 47 is expanded the plates 25~28 in the left-hand side of the drawing are rotated in the "clockwise direction" axis of the fixed side pivots APu(j) and APd(j) and the plates 29~32 in the right-hand side of the drawing are rotated in the "counter-clockwise direction" axis of the fixed side pivots APu(j) and APd(j).

For this reason, the up-and-down traveling distance of the ring end face presser bars 33~40 substantially coincides with the width of the belt laminated band 2 seeing that they are attached to the plates 25~32. Accordingly, with the ring end face presser bars 33~40 situated on both sides of the belt laminated band 2, these ring end face presser bars 33~40 can be rotated in the same axis of the pivot points APu(j) and APd(j).

Therefore, as shown in the drawing the end faces of the belt laminated band 2 can be can be shifted diagonally (slantwise) and exposed extensively (expanded wider) in a different tiered shape (the second process in the above-mentioned first embodiment) and further maintained in the same tiered state. Inspection of both end face surfaces of the belt laminated band 2 can be performed using the 1$^{st}$ end face defect inspection part 48 and the 2$^{nd}$ end face defect inspection part 49 (the third process in the above-mentioned first embodiment).

Otherwise, as shown in FIG. 6, when the shaft 47 of the up-and-down drive mechanism 46 is contracted to the minimum, the link 45 for angular adjustment moves to the "lowermost position." At this stage because the four movable pillars 41~44 are installed upright by both sides of the link 45 for angular adjustment and follow the downward movement of the link 45, these movable pillars 41~44 also move in the same direction.

The pivots APu(j) and APd(j) are respectively provided in the movable pillars 41~44 and one end side of the plates 25~32 is attached to the freely rotatable pivots APu(j) and APd(j). Further, since the other end side is respectively supported by the freely rotatable pivots KPu(i) and KPd(i) of the fixed pillars 21~24, ultimately the plates 25~32 will rotate in the axis of the fixed side pivot points APu(j) and APd(j) following the upward movement of the movable pillars 41~44.

Namely, when the shaft 47 is contracted, the plates 25~28 on the left-hand side of the drawing are rotated in the "counter-clockwise direction" axis of the fixed side pivots APu(j) and APd(j) and the plates 29~32 in the right-hand side of the drawing are rotated in the "clockwise direction" axis of the fixed side pivots APu(j) and APd(j).

For this reason, the up-and-down traveling distance of the ring end face presser bars 33~40 substantially coincides with the width of the belt laminated band 2 seeing that they are attached to the plates 25~32. Accordingly, with the ring end face presser bars 33~40 situated on both sides of the belt laminated band 2, these ring end face presser bars 33~40 can be rotated in the same axis of the pivot points APu(j) and APd(j).

Therefore, as shown in the drawing, the end faces of the belt laminated band 2 can be can be shifted diagonally (slantwise) and exposed extensively (expanded wider) in a different tiered shape (the second process in the above-mentioned first embodiment) and further maintained in the same tiered state. Inspection of both end face surfaces of the belt laminated band 2 can be performed using the $1^{st}$ end face defect inspection part 48 and the $2^{nd}$ end face defect inspection part 49 (the third process in the above-mentioned first embodiment).

As explained above, based on the embodiment of the metal ring inspection device 11, automation of the three processes in the above-stated first embodiment can be achieved.

In addition, although the above-stated explanation only describes two movement conditions of frame 16 for the inner periphery rollers by way of the uppermost position and the lowermost position, the present invention is not restricted to this. There may be a discretionary position between the uppermost position and the lowermost position. As the diagonal direction shift amount of the belt laminated band 2 end faces is regulated by the angle of the ring end face presser bars 33~40 and as this angle can be definably controllable by the up-and-down position of frame 16 for the inner periphery rollers, what is necessary is just to be able to freely determine the up-and-down position of frame 16 for the inner periphery rollers in proportion to a preferred shift.

Moreover, in this manner even when varying the angle of the ring end face presser bars 33~40 between the uppermost position and the lowermost position, because these ring end face presser bars 33~40 and the $1^{st}$ & $2^{nd}$ end face defect inspection parts 48, 49 are respectively attached to the common plates 25 & 26, 31 & 32, the inspectable surface angle of the $1^{st}$ & $2^{nd}$ end face defect inspection parts 48, 49 does not become unsuitable.

Furthermore, the technical concept of the metal ring inspection device related to the present invention is not limited to this second embodiment. What is essential is to constitute a configuration which can achieve automation of the three processes explained in the above-mentioned first embodiment.

Third Embodiment

Figure 7:
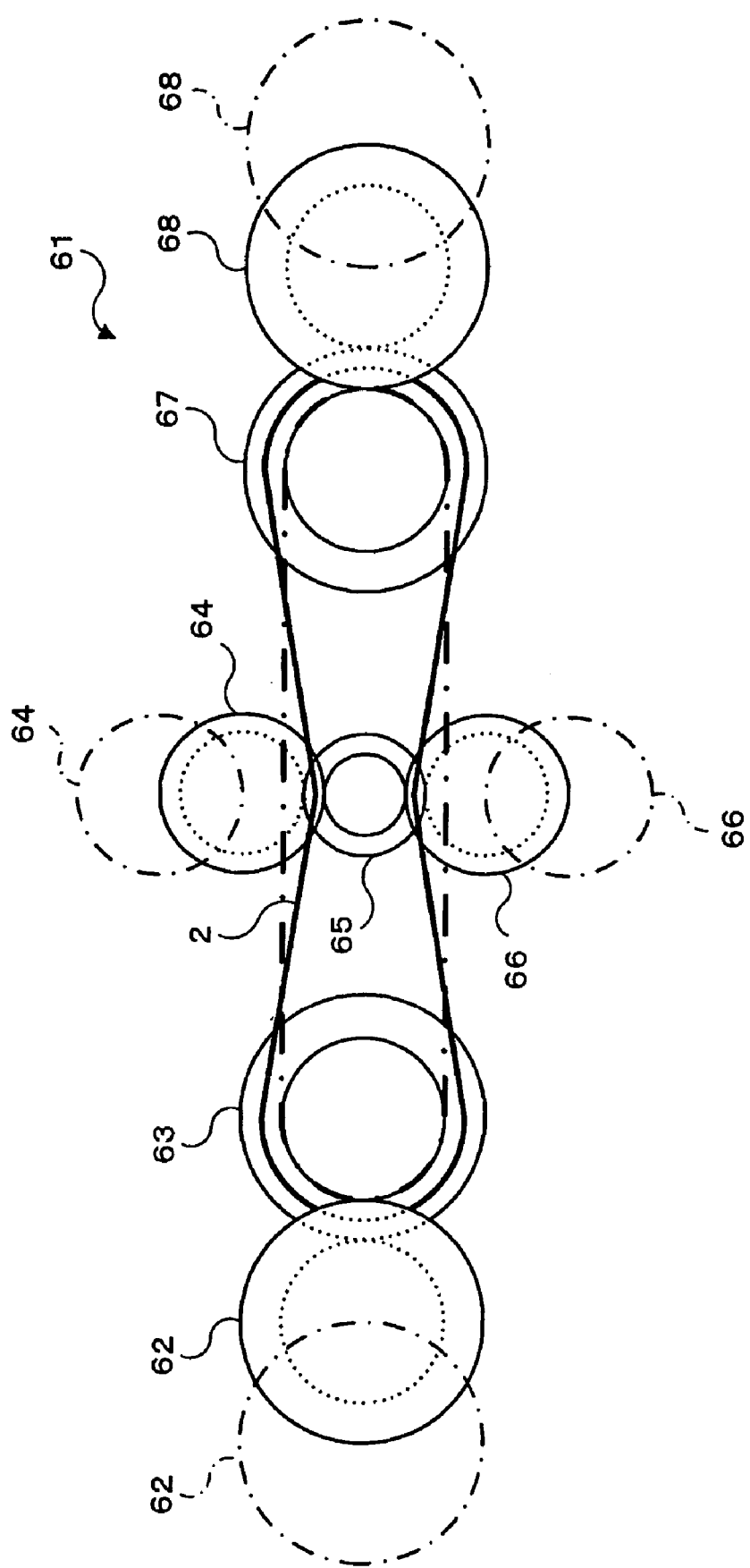
FIG. 7 is a top view of the third embodiment.
Figure 8A:
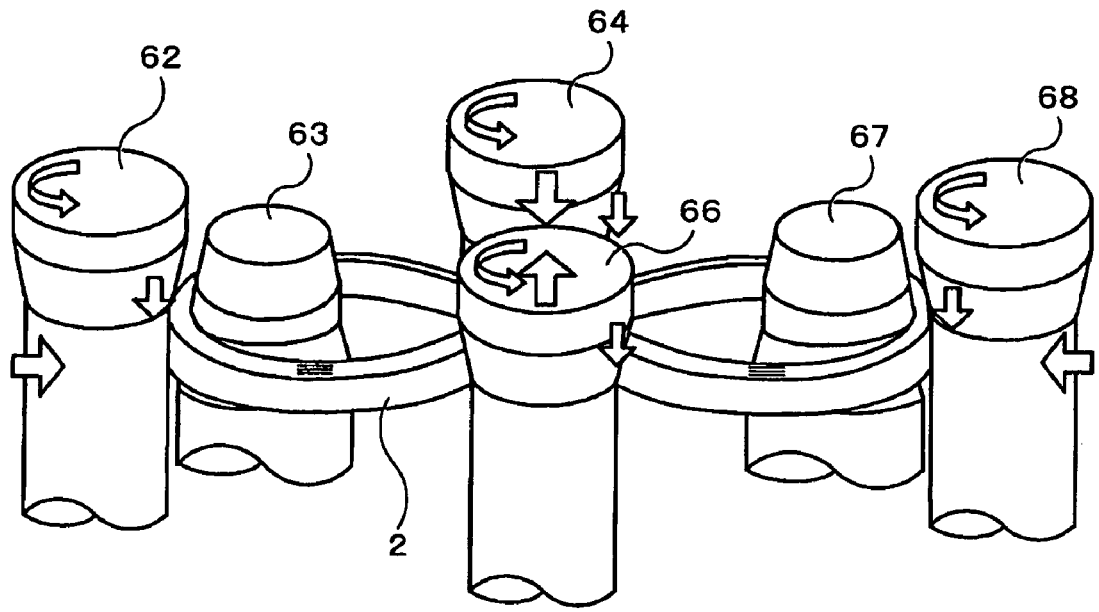
FIG. 8 is a perspective diagram of the third embodiment.
Figure 8B:
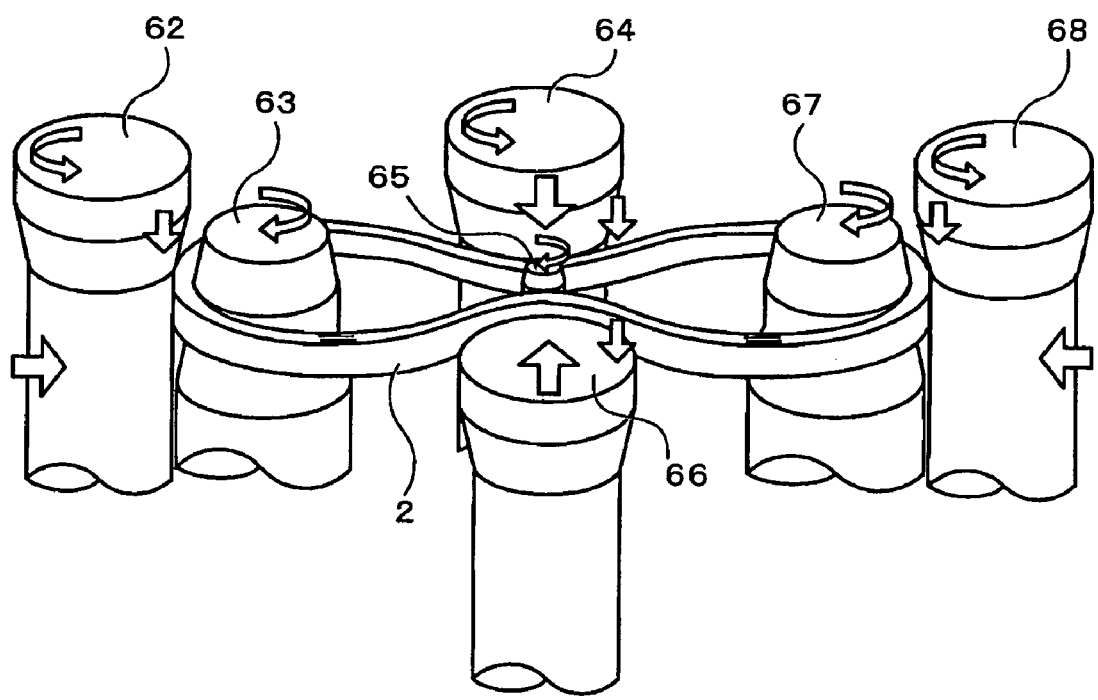
Figure 9:
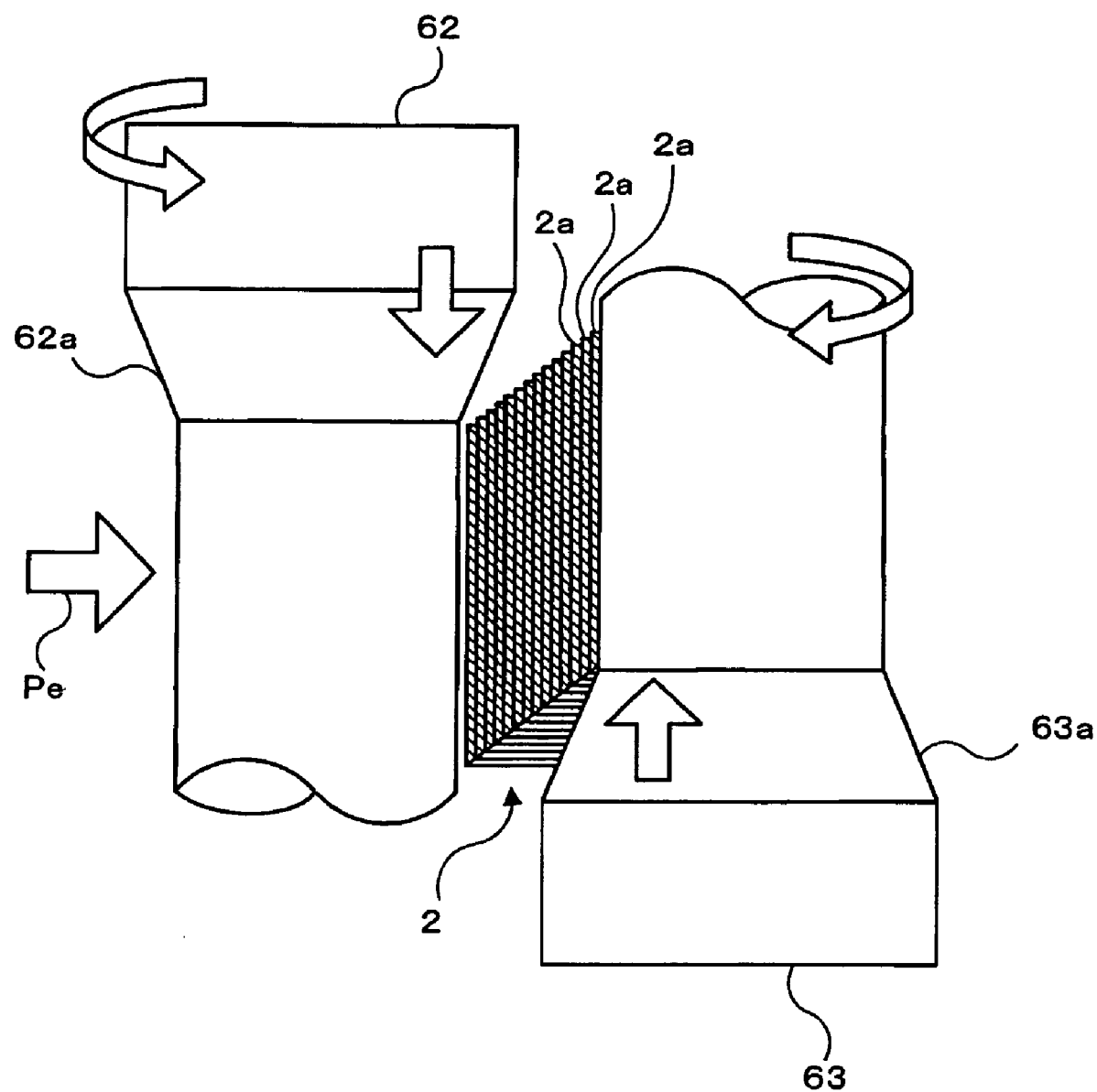
FIG. 9 is a main enlarged view of the third embodiment.
Figure 10:
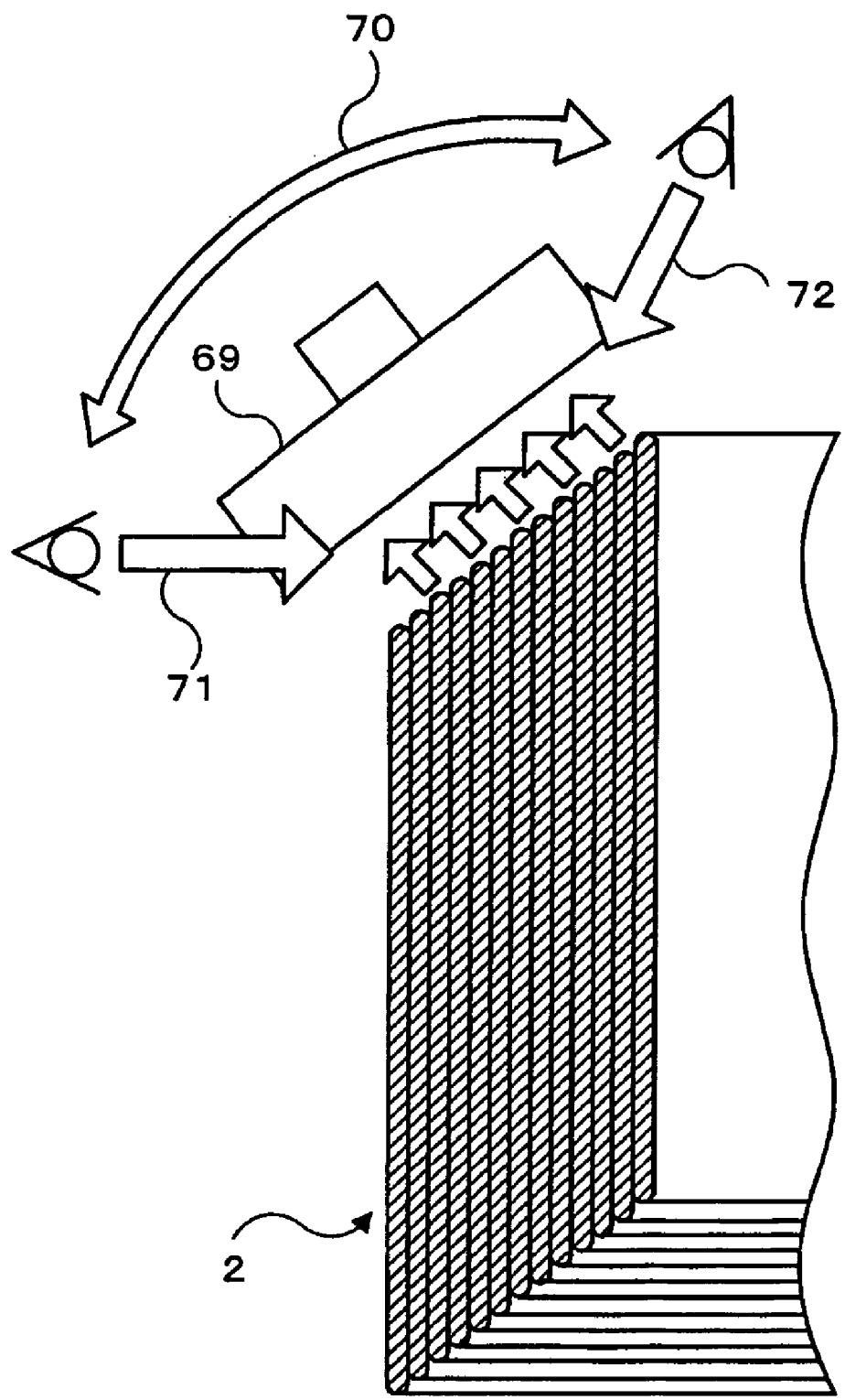
FIG. 10 is an end face defect inspection diagram of the third embodiment.
Figure 11A:
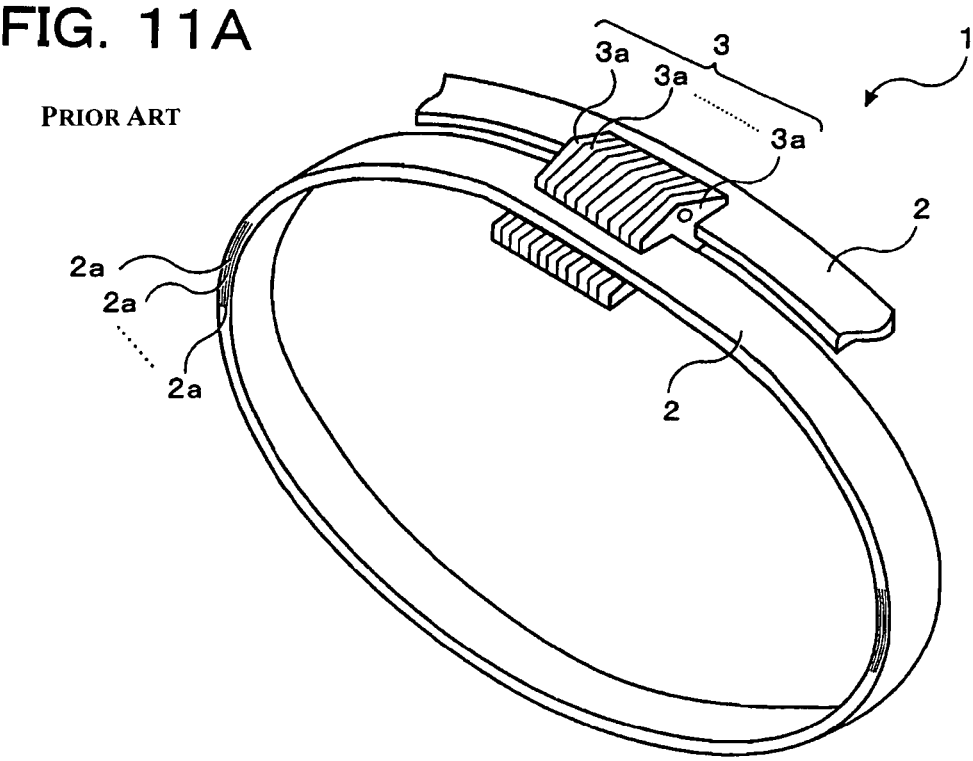
Figure 11B:
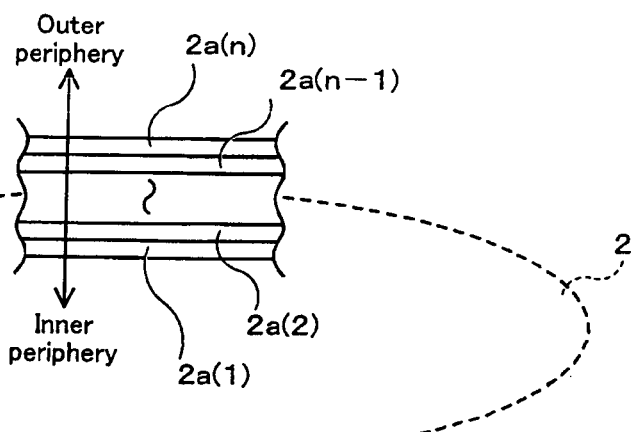
Figure 11C:
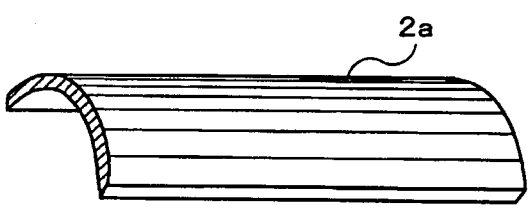
Figure 11D:
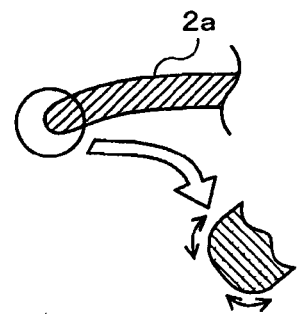
Figure 12:
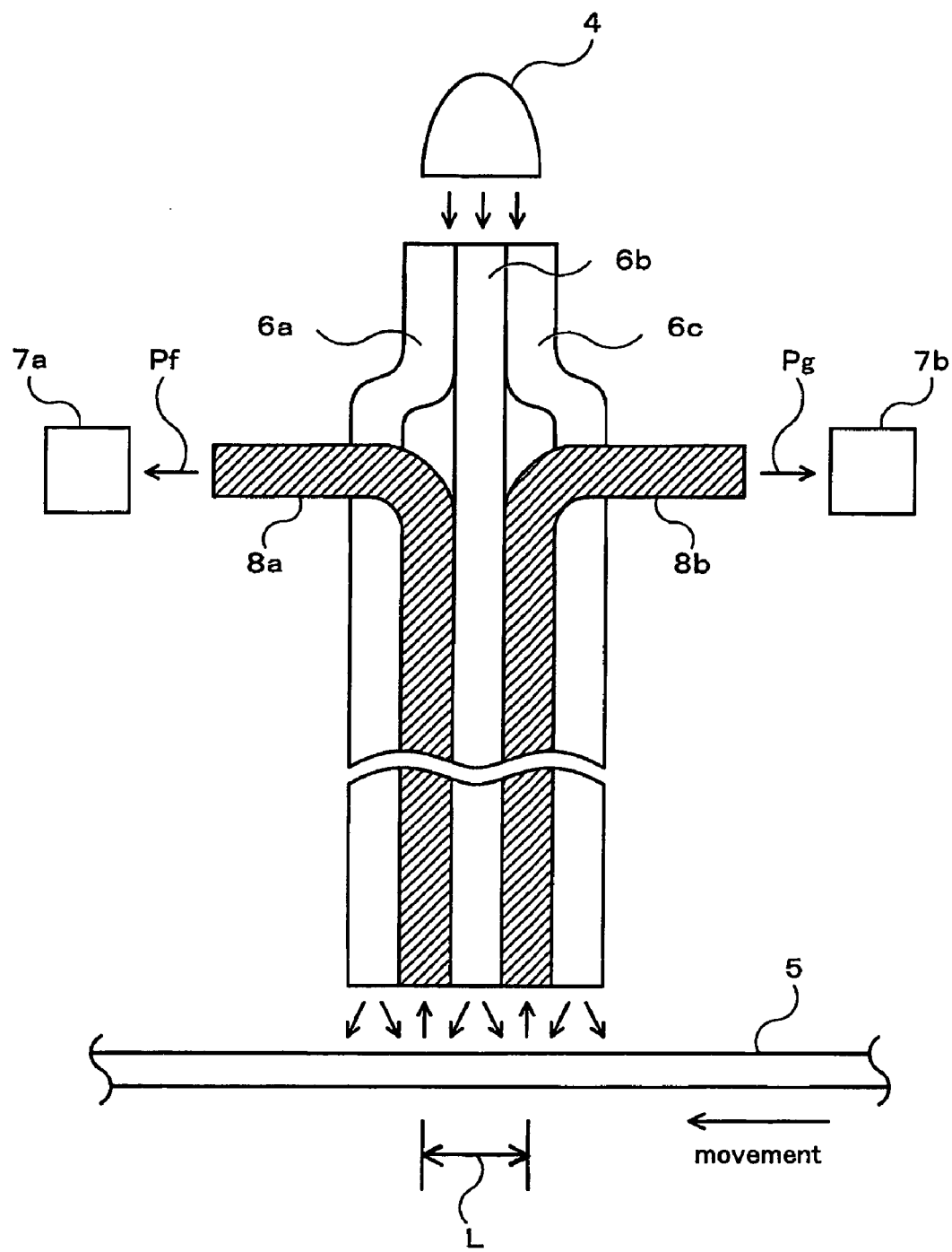
FIG. 12 is a conceptual configuration diagram of a conventional prior art device.

FIGS. 7~10 are diagrams showing another embodiment (hereinafter denoted as the "third embodiment") of the "metal ring inspection device" related to the present invention. FIG. 7 is a top view, FIG. 8 is a perspective diagram, FIG. 9 is a main enlarged view and FIG. 10 is an end face defect inspection diagram.

Referring now to FIG. 7, a metal ring inspection device 61 comprises seven rollers 62~68 (crowning removal means) which hold and rotate the inner and outer periphery surfaces of the belt laminated band 2 composing stacked n sheets of the metal rings 2a. The rollers 62, 64, 66 and 68 are position variable rollers. These rollers 62, 64, 66 and 68 travel between an initial position (the position at the time of mounting the belt laminated band 2) shown as a point difference line and an inspection position (the position when inspecting the end face defects of the belt laminated band 2). The roller 62 and the roller 63; the roller 64 and the roller 65; the roller 66 and the roller 65; and the roller 67 and the roller 68 are relatively displaced in the axis direction which mutually touch the outer peripheries during an inspection, respectively.

Referring to FIG. 8, all of the rollers 62~68 have a taper on the outer periphery surface. These tapers form surfaces in parallel where the taper of a roller in one direction and the taper of a roller in the opposite direction come in contact with each other. Here, the "taper" in the specification of the device can be said to gradually change the diameter of the roller axial direction. However, the present invention is not limited to the device illustrated in the diagrams and the device described in the specification.

In FIG. 9 for example, when the roller 62 and the roller 63 are used as an example explanation, one direction of the roller 62 outer periphery surface is formed with a taper 62a (end face exposure means) which becomes narrower on the lower side (decreases gradually as the diameter of the axis direction faces downward). Also, the opposite direction of the roller 63 outer periphery surface is formed with a taper 63a (end face exposure means) which becomes narrower on the upper side (decreases gradually as the diameter of the axis direction faces upward). These two tapers 62a, 63a are mutually parallel. Accordingly, by performing a downward shift of the roller 62 and an upward shift of the roller 63 while applying pressure Pe to move roller 62 closer to the direction of the roller 63 in a state that the belt laminated band 2 is grasped between the rollers 62, 63, the crowning in the metal rings 2a configuration of the belt laminated band 2 is removed and these metal rings 2a can then slide sideways. Besides, in the downward shift of the roller 62 and the upward shift of the roller 63 theoretically only one direction needs to be executed.

Referring now to FIG. 8, FIG. 8A is a state diagram at the time of removing the metal rings 2a crowning in the configuration of the belt laminated band 2. FIG. 8B is a state diagram at the time of making the metal rings 2a produce a slide sideways after removing crowning.

Specifically, in FIG. 8A the belt laminated band 2 is grasped between the rollers 62, 63; between the rollers 64, 65 (roller 65 is hidden behind roller 66 and not visible); between the rollers 65, 66; and between the rollers 67, 68. At this instant, the pressure Pe is applied between each of the rollers and crowning of the metal rings 2a is removed.

Then, in this condition (state in which the pressure Pe is applied) as shown in FIG. 8B, simultaneously the up-and-down motion of all the roller pairs, for example, the downward movement of the roller 62 and the upward movement of the roller 63; the downward movement of the roller 64 and the upward movement of the roller 65; the upward movement of the roller 65 and the downward movement of the roller 66; the upward movement of the roller 67 and the downward movement of the roller 68 is performed simultaneous in parallel. Thus, the belt laminated band 2 grasped between the taper of these rollers can be made to generate slide sideways. Also, as explained earlier, the up-and-down movement of the roller pairs of only one direction needs to be executed.

In this manner, by using a plurality of the rollers 62~68 which have a tapered shape like the above-mentioned second embodiment, the crowning in the metal rings 2a of a stacked layer state can be removed and these metal rings 2a can then slide sideways. Thus, the end face defects of the metal rings 2a in a slid sideways state can be automatically inspected with the end face defect inspection device which adapts the technique for example, as disclosed in Japanese Laid-Open Patent Application No. H11-248637 (1999) titled "DEFECT DETECTING DEVICE."

FIG. 10 is a defect inspection diagram. In this drawing, an end face defect inspection device 69 is arranged in parallel with the metal rings 2a end faces in a "slid sideways" state. Otherwise, as seen in the white arrow 70, the end face defect inspection device 69 scans at a predetermined angle and the metal rings 2a end faces are inspected. Moreover, the end face defects may be inspected by visual observation without using the end face defect inspection device 69. Specifically, as illustrated in the drawing, the metal rings 2a end faces which are in a slid sideways state can be observed from the preferred directions 71, 72. The presence of an end face defect can then be judged based on the differences in gloss, etc.

Also, in the metal ring inspection device 61 of the embodiment, automation of the three processes in the above-stated first embodiment can be achieved.

While the present invention has been described with reference to the preferred embodiments, it is intended that the invention be not limited by any of the details of the description therein but includes all the embodiments which fall within the scope of the appended claims.

What is claimed is:

1. A metal ring inspection method of a Continuously Variable Transmission (CVT) V-belt for inspecting end face defects in a belt laminated band comprised of a plurality of metal ring stacked layers in which:
   a first process is executed which gives the inner periphery surface of said belt laminated band a counter force while pressing the outer periphery surface of said belt laminated band from both sides and temporarily removes crowning from said metal rings;
   a second process is executed which applies a sliding force in the width direction relative to each metal ring comprising said belt laminated band to expose the end face of said belt laminated band in a different tiered shape; and
   a third process is subsequently executed which inspects said belt laminated band end face defects exposed in a different tiered shape.

2. A metal ring inspection device of a Continuously Variable Transmission (CVT) V-belt for inspecting end face defects in a belt laminated band composed of a plurality of metal ring stacked layers comprising:
   a crowning removal means which grasps the outer periphery surface of said belt laminated band from both sides so as to be firmly in contact with the inner periphery surface and removes crowning from said metal rings;
   an end face exposure means which applies a sliding force in the width direction relative to each metal ring after crowning removal and exposes said belt laminated band end face in a different tiered shape; and
   an inspection means which inspects said belt laminated band end face defects exposed in a different tiered shape.

3. The metal ring inspection device according to claim 2, wherein said crowning removal means removes crowning from said metal rings with a configuration including a plurality of rollers situated around said belt laminated band in which the position of each roller is shifted to increase pressure applied to the outer periphery surface of said belt laminated band.

4. The metal ring inspection device according to claim 2, wherein said crowning removal means removes crowning from said metal rings with a configuration including at least a pair of rollers which grasp and rotate between said belt laminated band to increase the pressing force between a pair of rollers.

5. The metal ring inspection device according to claim 2, wherein said end face exposure means has a configuration including at least a pair of ring end face presser bars which abut with both sides of said belt laminated band to adjust the angle of said ring end face presser bars and apply a sliding force in the width direction relative to each metal ring after crowning removal to expose said belt laminated band end face in a different tiered shape.

6. The metal ring inspection device according to claim 2, wherein said end face exposure means has a configuration including a taper formed in at least one pair of rollers which grasp and rotate between said belt laminated band according to the relative movement of the taper and apply a sliding force in the width direction relative to each metal ring after crowning removal to expose said belt laminated band end face in a different tiered shape.

7. A metal ring inspection device of a Continuously Variable Transmission (CVT) V-belt for inspecting end face defects in a belt laminated band composed of a plurality of metal ring stacked layers comprising:
   a crowning removal means which grasps the outer periphery surface of said belt laminated band from both sides so as to be firmly in contact with the inner periphery surface and removes crowning from said metal rings;
   an end face exposure means which applies a sliding force in the width direction relative to each metal ring after crowning removal and exposes said belt laminated band end face in a different tiered shape; and
   an inspection means which inspects said belt laminated band end face defects exposed in a different tiered shape,
   wherein said crowning removal means removes crowning from said metal rings with a configuration including a plurality of rollers situated around said belt laminated band in which the position of each roller is shifted to increase pressure applied to the outer periphery surface of said belt laminated band.

8. A metal ring inspection device of a Continuously Variable Transmission (CVT) V-belt for inspecting end face defects in a belt laminated band composed of a plurality of metal ring stacked layers comprising:
   a crowning removal means which grasps the outer periphery surface of said belt laminated band from both sides so as to be firmly in contact with the inner periphery surface and removes crowning from said metal rings;
   an end face exposure means which applies a sliding force in the width direction relative to each metal ring after crowning removal and exposes said belt laminated band end face in a different tiered shape; and an inspection means which inspects said belt laminated band end face defects exposed in a different tiered shape, wherein said end face exposure means has a configuration including at least a pair of ring end face presser bars which abut with both sides of said belt laminated band to adjust the angle of said ring end face presser bars and apply a sliding force in the width direction relative to each metal ring after crowning removal to expose said belt laminated band end face in a different tiered shape.

9. A metal ring inspection device of a Continuously Variable Transmission (CVT) V-belt for inspecting end face defects in a belt laminated band composed of a plurality of metal ring stacked layers comprising:

a crowning removal means which grasps the outer periphery surface of said belt laminated band from both sides so as to be firmly in contact with the inner periphery surface and removes crowning from said metal rings;

an end face exposure means which applies a sliding force in the width direction relative to each metal ring after crowning removal and exposes said belt laminated band end face in a different tiered shape; and an inspection means which inspects said belt laminated band end face defects exposed in a different tiered shape, wherein said end face exposure means has a configuration including a taper formed in at least one pair of rollers which grasp and rotate between said belt laminated band according to the relative movement of the taper and apply a sliding force in the width direction relative to each metal ring after crowning removal to expose said belt laminated band end face in a different tiered shape.

\* \* \* \* \*